(12) United States Patent
Zhao et al.

(10) Patent No.: US 10,011,559 B2
(45) Date of Patent: Jul. 3, 2018

(54) PREPARATION OF CHIRAL AMIDES AND AMINES

(71) Applicant: SUNOVION PHARMACEUTICALS INC., Marlborough, MA (US)

(72) Inventors: Hang Zhao, Westborough, MA (US); Stefan G. Koenig, Shrewsbury, MA (US); Charles P. Vandenbossche, Waltham, MA (US); Surendra Singh, Shrewsbury, MA (US); Harold Scott Wilkinson, Westborough, MA (US); Roger P. Bakale, Malverne, PA (US)

(73) Assignee: SUNOVION PHARMACEUTICALS INC., Marlborough, MA (US)

( * ) Notice: Subject to any disclaimer, the term of this patent is extended or adjusted under 35 U.S.C. 154(b) by 0 days.

(21) Appl. No.: 15/498,726

(22) Filed: Apr. 27, 2017

(65) Prior Publication Data
US 2018/0016224 A1    Jan. 18, 2018

Related U.S. Application Data

(60) Continuation of application No. 14/714,892, filed on May 18, 2015, which is a continuation of application No. 13/956,765, filed on Aug. 1, 2013, now abandoned, which is a continuation of application No. 13/333,616, filed on Dec. 21, 2011, now Pat. No. 8,524,950, which is a division of application No. 12/281,819, filed as application No. PCT/US2007/065659 on Mar. 30, 2007, now Pat. No. 8,097,760.

(60) Provisional application No. 60/787,837, filed on Mar. 31, 2006.

(51) Int. Cl.
| | | |
|---|---|---|
| *C07C 231/14* | (2006.01) |
| *C07C 249/08* | (2006.01) |
| *C07C 209/62* | (2006.01) |
| *C07C 231/12* | (2006.01) |
| *C07C 209/50* | (2006.01) |
| *C07C 211/42* | (2006.01) |
| *C07B 43/06* | (2006.01) |

(52) U.S. Cl.
CPC ............ *C07C 231/14* (2013.01); *C07B 43/06* (2013.01); *C07C 209/50* (2013.01); *C07C 209/62* (2013.01); *C07C 211/42* (2013.01); *C07C 231/12* (2013.01); *C07C 249/08* (2013.01); *C07C 2602/10* (2017.05)

(58) Field of Classification Search
None
See application file for complete search history.

(56) References Cited

U.S. PATENT DOCUMENTS

2004/0092605 A1* 5/2004 Jerussi ................. C07C 211/42
514/657

\* cited by examiner

*Primary Examiner* — Sudhakar Katakam
*Assistant Examiner* — Jennifer C Sawyer
(74) *Attorney, Agent, or Firm* — Heslin Rothenberg Farley & Mesiti P.C.; Nathan B. Davis

(57) ABSTRACT

This invention provides a convenient method for converting oximes into enamides. The process does not require the use of metallic reagents. Accordingly, it produces the desired compounds without the concomitant production of a large volume of metallic waste. The enamides are useful precursors to amides and amines. The invention provides a process to convert a prochiral enamide into the corresponding chiral amide. In an exemplary process, a chiral amino center is introduced during hydrogenation through the use of a chiral hydrogenation catalyst. In selected embodiments, the invention provides methods of preparing amides and amines that include the 1,2,3,4-tetrahydro-N-alkyl-1-naphthalenamine or 1,2,3,4-tetrahydro-1-naphthalenamine substructure.

6 Claims, No Drawings

PREPARATION OF CHIRAL AMIDES AND AMINES

CROSS REFERENCE TO RELATED APPLICATIONS

This application is a continuation of U.S. patent application Ser. No. 14,714,892, filed on May 18, 2015, which is a continuation of U.S. patent application Ser. No. 13/956,765, filed on Aug. 1, 2013, which is a continuation of U.S. patent application Ser. No. 13/333,616, filed on Dec. 21, 2011, now U.S. Pat. No. 8,524,950, which is a divisional of U.S. patent application Ser. No. 12/281,819, filed on Jan. 30, 2009, now U.S. Pat. No. 8,097,760, which is a 35 USC 371 national phase entry of International Patent Application Serial No. PCT/US2007/065659, filed on Mar. 30, 2007, which claims priority under 35 U.S.C. § 119(e) to U.S. Provisional Patent Application Ser. No. 60/787,837 filed on Mar. 31, 2006, each of which is incorporated herein by reference in its entirety for all purposes.

FIELD OF THE INVENTION

This invention relates to processes suitable for the large-scale preparation of enantiomerically- or diastereomerically-enriched chiral amides and amines prepared by these processes.

BACKGROUND OF THE INVENTION

Enantiomerically-enriched chiral primary amines are commonly used as resolving agents for racemic acids, as chiral auxiliaries for asymmetric syntheses and as ligands for transition metal catalysts used in asymmetric catalysis. In addition, many pharmaceuticals, such as sertraline, contain chiral amine moieties. Effective methods for the preparation of such compounds are of great interest to the pharmaceutical industry. Particularly valuable are processes that allow for the preparation of each enantiomer or diastereomer, in enantiomeric or diastereomeric excess, as appropriate, from prochiral or chiral starting materials.

Methods are available for the preparation of enantiomerically enriched amines. For example, the addition of organometallic reagents to imines or their derivatives is reported by Watanabe et al., *Tetrahedron Asymm.* (1995) 6:1531; Denmark et al., *J. Am. Chem. Soc.* (1987) 109:2224; Takahashi et al., *Chem. Pharm. Bull.* (1982) 30:3160; and the addition of organometallic reagents to chiral oxazolidines is disclosed by Mokhallalatiet et al., *Tetrahedron Lett.* (1994) 35:4267. Although some of these methods are widely employed, few are amenable to large-scale production of amines.

Other approaches involve optical resolution of a single enantiomer or diastereomer from a mixture. Resolution may be conducted through stereoselective biotransformations or by the formation of diastereomeric salts that are separated by crystallization. The utility and applicability of resolution methods relying on selective recrystallization are often limited by the lack of availability of appropriate chiral auxiliaries. In addition, resolution processes upon racemic mixtures afford a maximum yield of 50% for either stereoisomer. Therefore, the resolution of racemic mixtures is generally viewed as an inefficient process.

The preparation of an enantiomerically-enriched amine via conversion of a precursor oxime to the corresponding enamide, which is subsequently converted to the amine through asymmetric hydrogenation and deprotection, has been described (WO 99/18065 to Johnson et al.). The processes are, however, not of general applicability to a wide range of substrates. Moreover, many of the recognized processes require a large excess of metallic reagent to effect the conversion. The result is the generation of significant amounts of solid metal waste, a trait that is undesirable for large-scale production processes.

Therefore, a cost-efficient, scalable method for the conversion of oximes to corresponding enamides, which does not rely on a metallic reagent, is needed. The facile, high yield conversion of readily accessible oximes to the corresponding enamides without the use of metallic reagents would be a valuable step towards the large-scale synthesis of chiral amides and amines. The current invention addresses this and other needs.

SUMMARY OF THE INVENTION

The present invention provides an efficient and convenient method for the conversion of an oxime to the corresponding enamide. The method of the invention accomplishes the desired conversion without the use of a metallic reagent. The method is appropriate for large-scale synthesis of enamides, amides, amines, and their derivatives.

Thus, in a first aspect, the current invention provides a method for converting an oxime into an enamide. The method includes contacting the oxime with a phosphine and an acyl donor, under conditions appropriate to convert the oxime into the enamide. The method produces enamides in high yields and is generally applicable across a wide range of oxime structures. The enamides are readily converted to the corresponding amines. In an exemplary route, described in greater detail herein, the enamide is reduced to the corresponding amide, which is subsequently deacetylated to provide the amine.

The method is particularly useful for the large-scale synthesis of bioactive species, such as those having the 1,2,3,4-tetrahydro-N-alkyl-1-naphthalenamine or 1,2,3,4-tetrahydro-1-naphthalenamine substructure. Examples of bioactive compounds with this substructure include sertraline and sertraline analogs, and the trans isomers of sertraline, norsertraline and analogs thereof. Sertraline, (1S,4S)-cis 4-(3,4-dichlorophenyl)-1,2,3,4-tetrahydro-N-methyl-1-naphthalenamine, is approved for the treatment of depression by the United States Food and Drug Administration, and is available under the trade name ZOLOFT® (Pfizer Inc., NY, N.Y., USA). In human subjects, sertraline has been shown to be metabolized to (1S,4S)-cis 4-(3,4-dichlorophenyl)-1,2,3,4-tetrahydro-1-naphthalenamine, also known as desmethylsertraline or norsertraline.

Enamides provide a convenient precursor to compounds that include the 1,2,3,4-tetrahydro-N-alkyl-1-naphthalenamine or 1,2,3,4-tetrahydro-1-naphthalenamine substructure. Accordingly, in a second aspect, the present invention provides a method of converting an oxime having the formula:

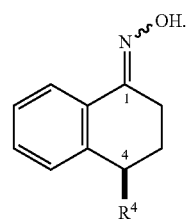

into an enamide having the formula:

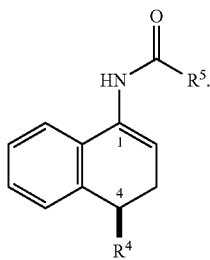

In the formulae above, the symbol $R^4$ represents substituted or unsubstituted aryl or substituted or unsubstituted heteroaryl. The symbol $R^5$ represents H, substituted or unsubstituted alkyl, substituted or unsubstituted heteroalkyl, substituted or unsubstituted aryl, substituted or unsubstituted heteroaryl or substituted or unsubstituted heterocycloalkyl. The method includes contacting said oxime with a phosphine and an acyl donor under conditions appropriate to convert said oxime to said enamide.

In a third aspect, the invention provides a mixture comprising:

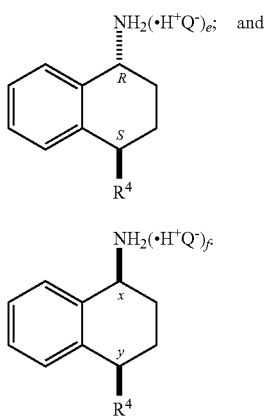

In the formulae above, $Q^-$ is an anion. The indices e and f are independently selected numbers from 0 to 1. The indices x and y independently represent (R) or (S). In an exemplary embodiment, when x is (R), y is (R) and when x is (S), y is (S). In another exemplary embodiment, when x is (S), y is (R).

The present invention provides a general and efficient method for converting oximes to enamides. Moreover, the invention provides a method for the stereoselective synthesis of sertraline and sertraline analogs, and the trans isomers of sertraline, norsertraline and analogs thereof. Additional objects, advantages and embodiments of the present invention are set forth in the detailed description that follows.

DETAILED DESCRIPTION OF THE INVENTION

Abbreviations

As used herein, "COD" means 1,5-cyclooctadiene.

Definitions

Where substituent groups are specified by their conventional chemical formulae, written from left to right, they equally encompass the chemically identical substituents, which would result from writing the structure from right to left, e.g., —$CH_2O$— is preferably intended to also recite —$OCH_2$—.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also preferably include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species. Alkyl groups are preferably substituted, e.g., with one or more groups referred to hereinbelow as an "alkyl group substituent."

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Two or more heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent refers to a substituted or unsubstituted divalent heteroalkyl radical, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents —C(O)$_2$R'— and, preferably, —R' C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

For brevity, the term "aryl" when used in combination with other terms (e.g., aryloxy, arylthioxy, arylalkyl) preferably includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$ in a number ranging from zero to (2m'+1), where m' is the total number of carbon atoms in such radical. R',R'', R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R'', —SR', —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R'', R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR''R''')$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate, and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. Hydrates of the salts are also included.

When the compound prepared by a method of the invention is a pharmacological agent, the salt is preferably a pharmaceutically acceptable salt. Examples of pharmaceutically acceptable salts are presented hereinabove, and are generally known in the art. See, for example, Wermuth, C., PHARMACEUTICAL SALTS: PROPERTIES, SELECTION AND USE—A HANDBOOK, Verlag Helvetica Chimica Acta (2002)

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogs. Other examples of prodrugs include compounds that comprise NO, NO$_2$, —ONO, or —ONO$_2$ moieties. The term "prodrug" is accorded a meaning herein such that prodrugs do not encompass the parent compound of the prodrug. When used to describe a compound of the invention, the term "prodrug" may also interpreted to exclude other compounds of the invention.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

As used herein, and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein, the term "substantially free of its cis stereoisomer" means that a mixture of a compound is made up of a significantly greater proportion of its trans stereoisomer than of its optical antipode. In a preferred embodiment of the invention, the term "substantially free of its cis stereoisomer" means that the compound is made up of at least about 90% by weight of its trans stereoisomer and about 10% by weight or less of its cis stereoisomer. In a more preferred embodiment of the invention, the term "substantially free of its cis stereoisomer" means that the compound is made up of at least about 95% by weight of its trans stereoisomer and about 5% by weight or less of its cis stereoisomer. In an even more preferred embodiment, the term "substantially free of its cis stereoisomer" means that the compound is made up of at least about 99% by weight of its trans stereoisomer and about 1% or less of its cis stereoisomer.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and "diastereomeric excess" are used interchangeably herein. Compounds with a single stereocenter are referred to as being present in "enantiomeric excess." Those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, e.g., tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

The present invention provides a non-metal mediated method for the conversion of oximes to the corresponding enamides. The enamides are formed in high yields and purities, making them suitable substrates for homogeneous asymmetric hydrogenation, a process that affords enantiomerically-enriched amides. The amides can be deprotected to furnish enantiomerically-enriched amines. Either enantiomer of the amine may be obtained by this method. Ketones and aldehydes can thus be transformed into enantiomerically-enriched chiral amines. The process is amenable to large-scale production.

Methods

A. Oxime to Enamide

In a first aspect, the present invention provides a method for converting an oxime into an enamide. The method includes contacting the oxime with a phosphine and an acyl donor, under conditions appropriate to convert the oxime into the enamide. Exemplary conditions are set forth herein.

In one embodiment, the oxime of use in the method of the invention has the formula:

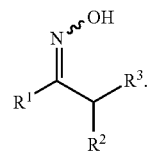

The symbols $R^1$, $R^2$ and $R^3$ represent radicals that are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. At least two of $R^1$, $R^2$ and $R^3$ are optionally joined to form a ring system selected from substituted or unsubstituted cycloalkyl, substituted or unsubstituted heterocycloalkyl, substituted or unsubstituted aryl and substituted or unsubstituted heteroaryl.

In another exemplary embodiment, the oxime has the formula:

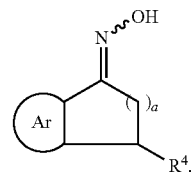

The symbol Ar represents substituted or unsubstituted aryl or substituted or unsubstituted heteroaryl. $R^4$ is H, substituted or unsubstituted alkyl, substituted or unsubstituted heteroalkyl, substituted or unsubstituted aryl, substituted or unsubstituted heteroaryl or substituted or unsubstituted heterocycloalkyl. The index a is an integer from 1 to 4.

In an exemplary embodiment according to this aspect, $R^4$ is substituted or unsubstituted aryl (e.g., phenyl). In a further exemplary embodiment, $R^4$ is phenyl substituted with at least one halogen atom.

In yet another exemplary embodiment, $R^4$ has the formula:

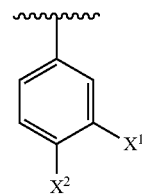

in which the symbols $X^1$ and $X^2$ represent independently selected halo moieties. In a preferred embodiment, $X^1$ and $X^2$ are each chloro.

In another exemplary embodiment, the oxime has the formula:

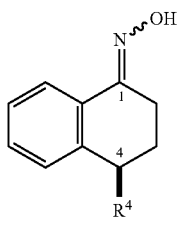

wherein R⁴ is selected from substituted or unsubstituted aryl and substituted or unsubstituted heteroaryl.

In a further exemplary embodiment, the oxime has the formula:

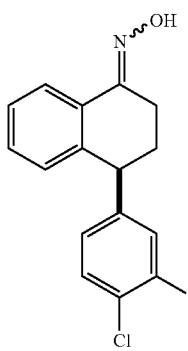

The preparation of oximes is well known in the art and a wide range of methods is known and readily practiced by those of skill in the art. Typically, oximes are prepared by reaction of ketones or aldehydes with hydroxylamine (or alkyloxyamine) under one of a variety of conditions. See, e.g., Sandler and Karo, "ORGANIC FUNCTIONAL GROUP PREPARATIONS," Vol. 3, pp 372-381, Academic Press, New York, 1972.

In an exemplary embodiment, optically pure tetralone is converted into the corresponding oxime according to Scheme 1.

Scheme 1

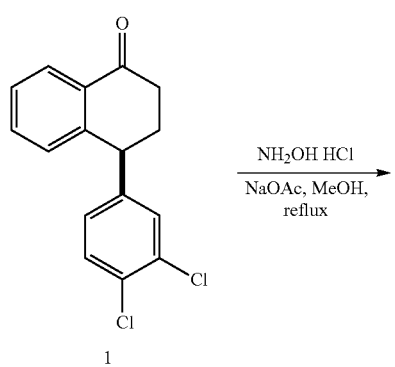

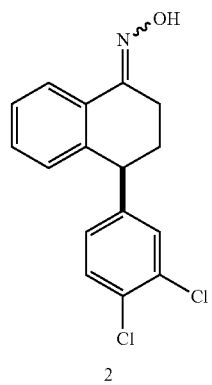

In Scheme 1, optically pure tetralone 1 is treated with hydroxylamine hydrochloride, and sodium acetate in methanol to afford the oxime 2. Compound 2 can either be isolated or carried forward as a solution in a suitable solvent to the next step. In another method, a ketone is converted to the corresponding oxime in an aromatic hydrocarbon solvent, e.g., toluene.

According to the process of the invention, the oxime is converted into an enamide. In an exemplary embodiment, the enamide has the formula:

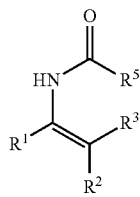

in which $R^1$-$R^3$ are as discussed above and $R^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

In another exemplary embodiment, the enamide has the formula:

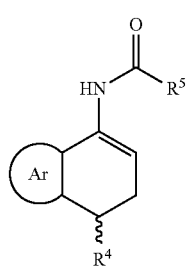

in which $R^4$ is selected from substituted or unsubstituted aryl and substituted or unsubstituted heteroaryl. $R^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

An exemplary enamide has the formula:

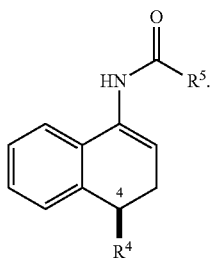

In an exemplary embodiment according to this aspect, C-4 of the ketone, oxime and enamide is of (S)-configuration.

In a preferred embodiment, the enamide has the formula:

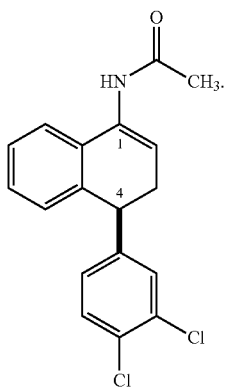 [SMILES: CC(=O)NC1=CC[C@@H](c2ccc(Cl)c(Cl)c2)c2ccccc21]

C-4 has a configuration selected from (R) and (S) and, in a preferred embodiment, C-4 is of (S)-configuration. In another embodiment, the method provides an enamide mixture including both (S)- and (R)-enantiomers.

Acyl Donor

Acyl donors of essentially any structure are of use in the present invention. An exemplary acyl donor has the formula:

Z—C(O)—R$^5$ in which Z is a leaving group. R$^5$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

In an exemplary embodiment, the acyl donor is an acid anhydride, in which Z has the formula:

R$^6$—C(O)—O— in which R$^6$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

In another exemplary embodiment, R$^5$ and R$^6$ are independently selected substituted or unsubstituted $C_1$-$C_4$ moieties.

In another exemplary embodiment, the acyl donor is an anhydride, preferably acetic anhydride ($Ac_2O$).

In another exemplary embodiment, the acyl donor is a member selected from an acid chloride (Z=Cl) and an activated ester, e.g., an N-hydroxy succinimidyl ester.

The acyl donor can be present in any useful amount and selection of this amount is within the abilities of those of skill in the art. In an exemplary embodiment, the acyl donor is used in an amount from about 1 to about 3 equivalents, preferably from about 1 to about 2 equivalents and, more preferably, from about 1 to about 1.5 equivalents relative to the oxime substrate.

Phosphine

Phosphorus reagents, such as phosphines, of any structure are of use in practicing the present invention. For example, in general, phosphines have the formula:

P(Q)$_3$ in which each Q is independently selected from H, substituted or unsubstituted alkyl and substituted or unsubstituted aryl.

In an exemplary embodiment, each Q is a member independently selected from substituted or unsubstituted $C_1$-$C_6$ alkyl and substituted or unsubstituted phenyl. Presently preferred phosphorus reagents include, but are not limited to, diphenylphosphine ($Ph_2PH$), triphenylphosphine ($Ph_3P$), tri-n-butylphosphine (n-$Bu_3P$), triethylphosphine ($Et_3P$), tri-n-propylphosphine (n-$Pr_3P$), 1,2-bisdiphenylphosphinoethane ($Ph_2PCH_2CH_2PPh_2$), diethyl phosphite ($Et_2OP(O)H$), triphenyl phosphite (($PhO)_3P$), P-chlorodiphenylphosphine ($Ph_2PCl$), methyltriphenylphosphonium bromide ($MePh_3PBr$), and benzyltriphenylphosphonium chloride ($BnPh_3PCl$).

The phosphorus reagent, such as phosphine, is incorporated into the reaction mixture in substantially any useful amount. Exemplary reactions of the invention utilize from about 0.5 equivalents to about 5 equivalents, preferably from about 1 equivalent to about 3 equivalents and, more preferably, from about 1.1 equivalents to about 2 equivalents of the phosphorus reagent with respect to the carbonyl-containing substrate.

Solvent

In an exemplary embodiment, the oxime is contacted with the phosphorus reagents (e.g., phosphine) and the acyl donor in the presence of an organic solvent. The solvent can be a protic or an aprotic solvent. In a preferred embodiment, the solvent is an aprotic solvent. In a further preferred embodiment, the aprotic solvent is an aromatic solvent (e.g., toluene, xylene and combinations thereof).

In an exemplary embodiment, in which the oxime is compound 3, the solvent is preferably toluene.

B. Enamide to Amide

In another aspect, the current invention provides a method for converting an enamide to an amide. The method includes, contacting the enamide with a hydrogenation catalyst and hydrogen or a hydrogen transfer reagent under conditions appropriate to hydrogenate a carbon-carbon double bond of the enamide, thereby converting the enamide to an amide.

The methods of the present invention are not limited to practice on enamides characterized by any particular structural element or membership within any single structural class. The methods disclosed herein are of broad applicability across a wide range of enamide structures. Exemplary reagents and reaction conditions for the conversion of the enamide to the amide are set forth below.

Catalyst

The carbon-carbon double bonds of the enamides are reduced by processes such as hydrogen transfer, in which a hydrogen-donor such as a secondary alcohol, and in particular isopropanol is used; and hydrogenation, in which molecular hydrogen is used. Both hydrogen transfer and hydrogenation processes require a catalyst or catalytic system to activate the reducing agent, namely an alcohol or molecular hydrogen, respectively.

In selected embodiments of the present invention, the enamide substrate is chiral or prochiral and the reduction, hydrogen transfer or hydrogenation is performed in a stereoselective manner. In this embodiment, it is generally preferred that the catalyst is a chiral catalyst. Also preferred is that the chiral catalyst is a transition metal catalyst.

Numerous reports have been published on chiral transition metal complex catalysts usable in catalytic asymmetric hydrogenation reactions. Among these, transition metal complexes of ruthenium, iridium, rhodium, palladium, nickel or the like, which contain optically active phosphines as ligands, have been reported to exhibit excellent performance as catalysts for asymmetric synthetic reactions, and some of them are already used in industrial application. See, e.g., ASYMMETRIC CATALYSIS IN ORGANIC SYNTHESIS, Ed., R. Noyori, Wiley & Sons (1994); and G. Franciò, et al., *Angewandte Chemie. Int. Ed.*, 39: 1428-1430 (2000).

In a preferred embodiment, the metal in the catalyst is rhodium (Rh), ruthenium (Ru) or iridium (Ir).

In an exemplary embodiment, the hydrogenation catalyst used in the present methods is a chiral complex of a transition metal with a chiral phosphine ligand, including monodentate and bidentate ligands. For example, preferred bidentate ligands include 1,2-bis(2,5-dimethylphospholano) ethane (MeBPE), P,P-1,2-phenylenebis {(2,5-endo-dimethyl)-7-phosphabicyclo[2.2.1]heptane} (MePennPhos), 5,6-bis(diphenylphosphino) bicyclo[2.2.1]hept-2-ene (NorPhos) and 3,4-bis(diphenylphosphino) N-benzyl pyrrolidine (commercially available as catASium® D).

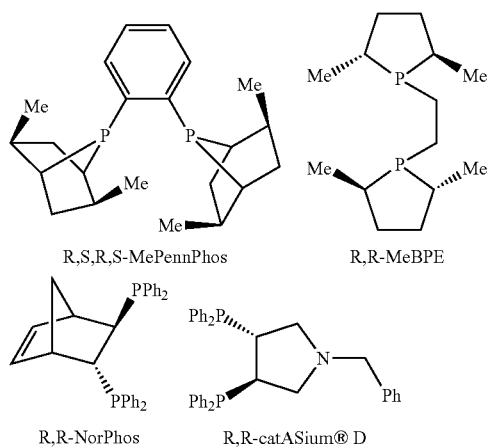

In a preferred embodiment for making the amide derived from tetralones, the chiral catalyst is (R,S,R,S)-MePennPhos (COD)RhBF$_4$, (R,R)-MeBPE(COD)RhBF$_4$, (R,R)-NorPhos (COD)RhBF$_4$ (Brunner et al., *Angewandte Chemie* 91(8): 655-6 (1979)), or (R,R)-catASium® D(COD)RhBF$_4$ (Nagel et al., *Chemische Berichte* 119(11): 3326-43 (1986)).

The catalyst is present in the reaction mixture in any useful amount. Determining an appropriate catalyst structure and an effective amount of this catalyst is well within the abilities of those skilled in the art. In an exemplary embodiment, the catalyst is present in an amount of from about 0.005 mol % to about 1 mol % Generally, it is preferred that the catalyst be present in an amount of from about 0.01 mol % to about 0.5 mol % and, even more preferably, from about 0.02 mol % to about 0.2 mol %.

In an exemplary embodiment, the enamide is hydrogenated to the corresponding amide in the presence of from about 0.02 to about 0.3 mol %, preferably, from about 0.03 to about 0.2 mol %, and even more preferably, from about 0.03 to about 0.1 mol % Rh-MeBPE catalyst.

In another exemplary embodiment, the enamide is hydrogenated to give the amide in the presence of about 0.1 to about 1.0 mol %, preferably about 0.1 to about 0.5 mol % and, more preferably about 0.3 mol % of a Rh-PennPhos catalyst.

In another exemplary embodiment, the enamide is hydrogenated to give the amide in the presence of about 0.005 to about 1.0 mol %, preferably about 0.01 to about 0.5 mol % and, more preferably about 0.02 to about 0.1 mol % of (R,R)-NorPhos(COD)RhBF$_4$ catalyst.

A presently preferred catalyst of use in the invention provides the amide in a high yield of at least 85%, preferably at least 90% and more preferably at least 95% yield from the enamide. A generally preferred catalyst is one that provides high yields of amides when the synthesis is on a large scale of at least 300 grams, preferably at least 500 grams, more preferably at least 750 grams and even still more preferably at least 1,000 g. Preferred catalysts provide the amides in the high yield set forth above when the reaction is carried out on the large scale, also set forth above. An exemplary catalyst having these desirable properties is (R,R)-NorPhos(COD) RhBF$_4$.

Hydrogen Pressure

When the conversion of the C—C double bond of the enamide to the corresponding C—C single bond is effected by hydrogenation, the pressure of the hydrogen in the reaction vessel can be adjusted to optimize the reaction yield and stereoselectivity. The methods of the invention are practiced with any useful hydrogen pressure, and those with skill in the art will understand how to adjust the hydrogen pressure to optimize the desired result.

In an exemplary embodiment, the enamide is hydrogenated, to afford the amide, at a hydrogen pressure of about 2 to about 10 bar, preferably about 4 to about 8 bar and, more preferably, about 5 to about 6 bar.

Solvent

The methods of the invention are not limited to practice with any one solvent or any class of solvents, e.g. protic, aprotic, aromatic, or aliphatic. Choice of an appropriate solvent for a particular reaction is well within the abilities of those of skill in the art.

In an exemplary embodiment, the enamide is converted to the amide in the presence of a solvent, which is a protic solvent, an aprotic solvent, or a mixture thereof. In a preferred embodiment the solvent is a protic solvent, which is an alcohol, more preferably, a $C_1$ to $C_4$-alcohol. In other preferred embodiments, the alcohol is methanol, ethanol, n-propanol, iso-propanol, n-butanol, 2-butanol, or 2,2,2-trifluoroethanol ($CF_3CH_2OH$). In a presently preferred embodiment, the alcohol is iso-propanol.

In another exemplary embodiment, the aprotic solvent is an aromatic solvent, a non-aromatic solvent or a mixture thereof. Exemplary aromatic solvents of use in the present invention include toluene, benzene, and xylene, and preferably less toxic aromatic solvents such as toluene and xylene. Exemplary non-aromatic solvents of use in the methods of the invention include tetrahydrofuran (THF), dichloromethane ($CH_2Cl_2$), ethyl acetate (EtOAc), and acetonitrile ($CH_3CN$).

The solvent and substrate are present in essentially any useful ratio. In an exemplary embodiment, the solvent and substrate are present in amounts that provide a substrate solution of from about 0.05 M to about 0.5 M, preferably, from about 0.1 M to about 0.3 M and, more preferably, from about 0.12 M to about 0.34 M.

Amide

The amides formed by the methods of the invention have diverse structures and can include alkyl, heteroalkyl, aryl and heteroaryl substructures. In an exemplary embodiment, the amide has the formula:

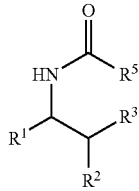

in which $R^1$-$R^3$ and $R^5$ are as discussed above.

As discussed previously, the methods of the invention are useful for preparing amides that include within their structure the 1,2,3,4-tetrahydro-N-alkyl-1-naphthalenamine or 1,2,3,4-tetrahydro-1-naphthalenamine substructure. Thus, in an exemplary embodiment, the amide has the formula:

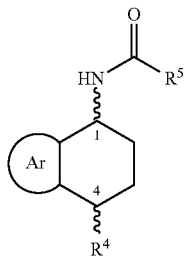

in which $R^4$ and $R^5$ are as described above.

An exemplary amide is a trans amide, having the formula:

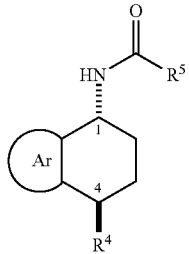

A further exemplary amide has the formula:

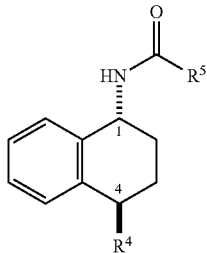

In a preferred embodiment, the amide has the formula:

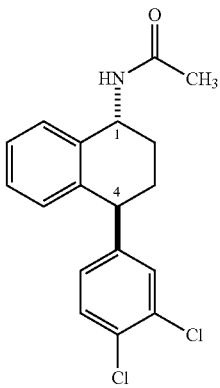

In each of the amide formulae above, C-1 and C-4 have a configuration independently selected from (R) and (S), and in a preferred embodiment, C-1 is of (R)-configuration, and C-4 is of (S)-configuration.

Enantiomeric or Diastereomeric Excess

In a preferred embodiment, the enantiomeric excess (ee) of a desired enantiomer or the diastereomeric excess (de) of a desired diastereomer produced by the present method is from about 60% ee/de to about 99% ee/de, preferably from about 70% ee/de to about 99% ee/de, more preferably, from about 80% ee/de to about 99% ee/de, still more preferably, from about 90% ee/de to about 99% ee/de.

In another preferred embodiment, the invention provides an amide having an enantiomeric or diastereomeric excess of at least about 99%, preferably, at least about 99.4% and, more preferably, at least about 99.8%. Amides that are essentially free of their optical antipodes are accessible through the methods of the invention.

When using rhodium catalyst systems based on chiral bidentate ligands, such as those derived from 1,2-bis(phospholano)ethane (BPE) ligands, P,P-1,2-phenylenebis(7-phosphabicyclo[2.2.1]heptane) (PennPhos) ligands, 5,6-bis(phosphino)bicyclo[2.2.1]hept-2-ene (NorPhos) ligands, or 3,4-bis(phosphino) pyrrolidine (commercially available as catASium® D) ligands, the diastereomeric purity of the trans amide derived from the corresponding enamide is surprisingly high.

In a preferred embodiment, when the amide includes the 1,2,3,4-tetrahydro-N-alkyl-1-naphthalenamine or 1,2,3,4-tetrahydro-1-naphthalenamine subunit, the method provides (1R,4S)-trans amide, which is substantially free of its cis isomer.

In one exemplary embodiment, the enamide is hydrogenated at about 4 to about 6 bar hydrogen pressure using about 0.03 to about 0.05 mol % of a Rh-Me-BPE catalyst in isopropanol, to give the trans N-acetyl amide in about 80 to about 99% de, preferably at least 95% de, and more preferably at least 99% de.

In another exemplary embodiment, the enamide is hydrogenated at about 4 to about 5 bar hydrogen pressure, using about 0.2 to about 0.5 mol % of a Rh-PennPhos catalyst in isopropanol, to give the trans N-acetyl amide in about 80 to about 99% de, preferably at least 95% de, and more preferably at least 99% de.

In yet another exemplary embodiment the enamide is hydrogenated at about 5 to about 8 bar hydrogen pressure, using about 0.01 to about 0.05 mol % of (R,R)NorPhos (COD)RhBF$_4$ catalyst in isopropanol to give the trans N-acetyl amide in about 80-99% de, preferably at least 95% de, and more preferably at least 99% de.

In a preferred embodiment, the hydrogenation is carried out at an enamide concentration of about 0.1 M to about 0.3 M.

In a further exemplary embodiment, the stereoisomerically enriched amide is purified, or further enriched, by selective crystallization. In another exemplary embodiment, the amide is purified, or enriched, to an enantiomeric or diastereomeric purity of about 90 to about 99% ee/de. In another exemplary embodiment, the amide is purified, or enriched, to an enantiomeric or diastereomeric purity of about 95 to about 99% ee/de.

The product of the hydrogenation or hydrogen transfer can be enantiomerically or diastereomerically enriched by methods known in the art, e.g., chiral chromatography, selective crystallization and the like. It is generally preferred that the enrichment afford a product at least about 95% of which is a single stereoisomer. More preferably, at least about 97%, still more preferably at least about 99% is a single stereoisomer.

In a presently preferred embodiment, the enriched trans amide is purified, or enriched, by selective crystallization, affording the desired trans isomer in about 99% de.

C. Amide to Amine

In another aspect, the current invention provides methods for converting an amide formed from the corresponding enamide to an amine. In an exemplary embodiment, the method includes contacting the amide with a deacylating reagent under conditions appropriate to deacylate the amide, thereby forming an amine.

In an exemplary embodiment, the amine has the formula:

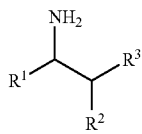

or a salt thereof. The radicals have the identities set forth above.

The amine can be of any desired structure, however, it is preferably a chiral amine. When the amine is chiral, the enantiomeric excess (ee) of a desired enantiomer or the diastereomeric excess (de) of a desired diastereomer produced by the present method is from about 60% ee/de to about 99% ee/de, preferably from about 70% ee/de to about 99% ee/de, more preferably, from about 80% ee/de to about 99% ee/de, still more preferably, from about 90% ee/de to about 99% ee/de.

In another preferred embodiment, the invention provides an amine having an enantiomeric or diastereomeric excess of at least about 99%, preferably, at least about 99.4% and, more preferably, at least about 99.8%. Amines that are essentially free of their optical antipodes are accessible through the methods of the invention.

In an exemplary embodiment, the amine includes the 1,2,3,4-tetrahydro-N-alkyl-1-naphthalenamine or 1,2,3,4-tetrahydro-1-naphthalenamine substructure, and has the formula:

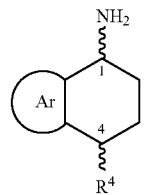

or a salt thereof.

In a preferred embodiment, the amine is a trans amine, having the formula:

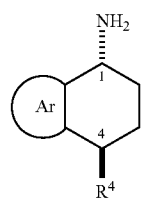

or a salt thereof.

An exemplary amine has the formula:

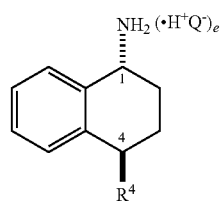

in which Q$^-$ is an anion. The index e is a number from 0 to 1. The index may take a fractional value, indicating that the amine salt is a hemi-salt.

In a preferred embodiment, the amine has the formula:

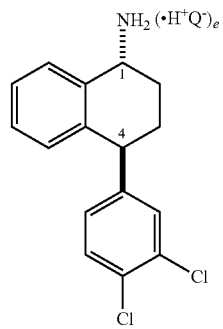

wherein Q$^-$ and e are as described above.

C-1 and C-4 have a configuration independently selected from (R) and (S). Preferably C-1 is of (R)-configuration, and C-4 is of (S)-configuration.

In another preferred embodiment, the amine is in the trans configuration and is substantially free of the cis isomer.

The amide is deacylated by any suitable process. Many methods of deacylating amides to the corresponding amines are known in the art. In an exemplary embodiment, the deacylating reagent is an enzyme. Exemplary enzymes of use in this process include those of the class EC 3.5.1 (e.g., amidase, aminoacylase), and EC 3.4.19.

In another embodiment, the deacylating reagent is an acid or a base. The acid or base can be either inorganic or organic. Mixtures of acids or mixtures of bases are useful as well. When the deacylating reagent is an acid, it is generally preferred that the acid is selected so that the acid hydrolysis produces a product that is a form of the amine. In an exemplary embodiment, the acid is hydrochloric acid (HCl).

Other deacylating conditions of use in the present invention include, but are not limited to, methanesulfonic acid/HBr in alcoholic solvents, triphenylphosphite/halogen (e.g., bromine, chlorine) complex and a di-t-butyl dicarbonate/lithium hydroxide sequence.

In a preferred embodiment, the amide is deacylated by treatment with an activating agent, e.g., trifluoromethanesulfonic anhydride, phosgene, and preferably, oxalyl chloride/pyridine. The reaction is quenched with an alcohol, preferably a glycol, e.g., propylene glycol.

When the amide includes the 1,2,3,4-tetrahydro-N-alkyl-1-naphthalenamine or 1,2,3,4-tetrahydro-1-naphthalenamine substructure, the deacylation conditions preferably are selected such that formation of any dihydronaphthalene side products are minimized.

The amine can be isolated or enriched. A currently preferred method of isolating or enriching the amine includes at least one step of selective crystallization.

The amine is optionally N-alkylated or N-acylated to prepare the corresponding N-alkyl or N-acyl derivative.

In an exemplary embodiment, the invention provides a method suitable for the large scale preparation of trans 4-(3,4-dichlorophenyl)-1,2,3,4-tetrahydro-1-naphthalenamine 5 and salt forms thereof. In an exemplary embodiment, the process involves the synthesis of an enamide, e.g. enamide 3, starting from optically pure (4S)-tetralone 1 via the oxime 2, and subjecting enamide 3 to catalytic asymmetric hydrogenation to afford amide 4, which upon N-deacylation affords trans 4-(3,4-dichlorophenyl)-1,2,3,4-tetrahydro-1-naphthalenamine 5, or a salt thereof (Scheme 2).

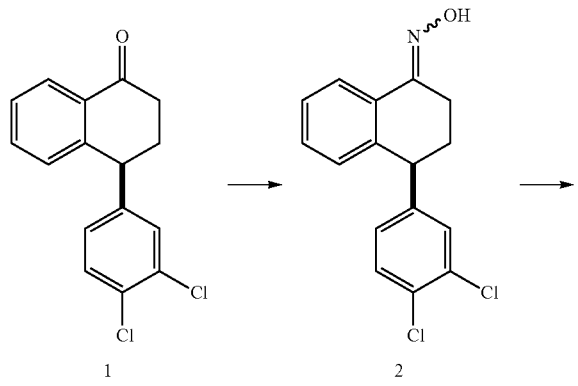

Scheme 2

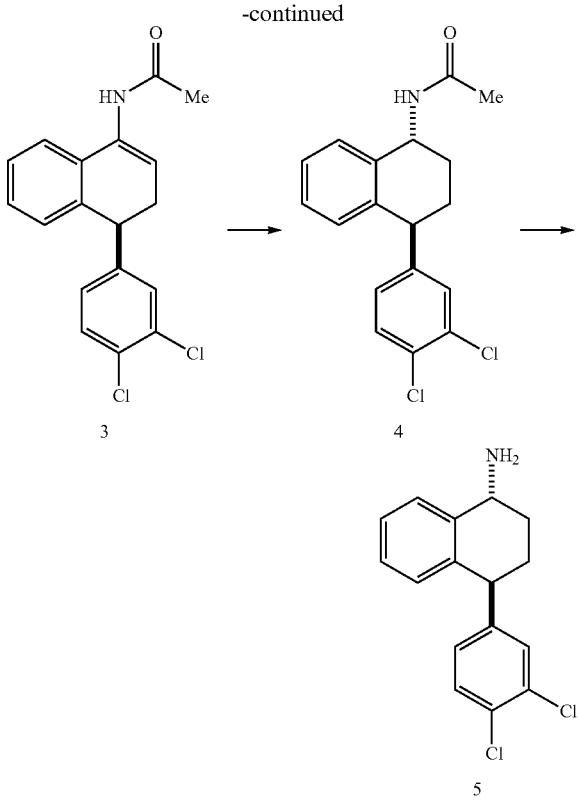

In a preferred embodiment, the compound prepared by the route of Scheme 2 is (1R,4S)-trans 4-(3,4-dichlorophenyl)-1,2,3,4-tetrahydro-1-naphthalenamine. Even more preferred is the preparation of the compound substantially free of its cis isomer.

Compounds according to formula 5 include stereoisomers of desmethylsertraline. The N-methyl analog of 5 is a stereoisomer of sertraline.

The primary clinical use of sertraline is in the treatment of depression. In addition, U.S. Pat. No. 4,981,870 discloses and claims the use of sertraline and related compounds for the treatment of psychoses, psoriasis, rheumatoid arthritis and inflammation.

(1R,4S)-trans 4-(3,4-dichlorophenyl)-1,2,3,4-tetrahydro-1-napthalenamine and (1S,4R)-trans 4-(3,4-dichlorophenyl)-1,2,3,4-tetrahydro-1-napthalenamine are useful in the treatment of CNS-related disorders that are modulated by monoamine activity (U.S. Patent Application No. 2004/0092605 to Jerussi et al.; cited references). Those CNS-related disorders include mood disorders (e.g. depression), anxiety disorders (e.g., OCD), behavioral disorders (e.g. ADD and ADHD), eating disorders, substance abuse disorders and sexual function disorders. Potentially, these molecules produce diminished side effects as compared to the current standards of treatment. The compounds are also useful for the prophylaxis of migraine.

IV. Compositions

In another aspect, the invention provides a mixture comprising:

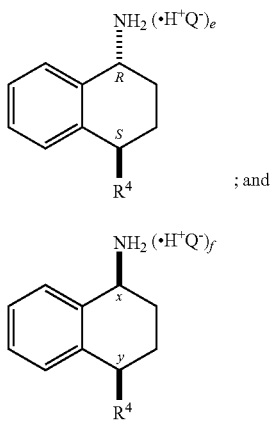

A

B in which R⁴ is a member selected from substituted or unsubstituted aryl and substituted or unsubstituted heteroaryl. Q⁻ is an anion. The indices e and f independently represent a number from 0 to 1. Thus, the structures above encompass hemi-salts.

The indices x and y are independently selected from (S) and (R). In one embodiment, when x is (S), y is (S) and when x is (R), y is (R). In another embodiment, when x is (S), y is (R).

In an exemplary embodiment, R⁴ is substituted or unsubstituted aryl. A preferred aryl moiety is a substituted or unsubstituted phenyl moiety.

In another exemplary embodiment, the mixture comprises compounds with the following formulae:

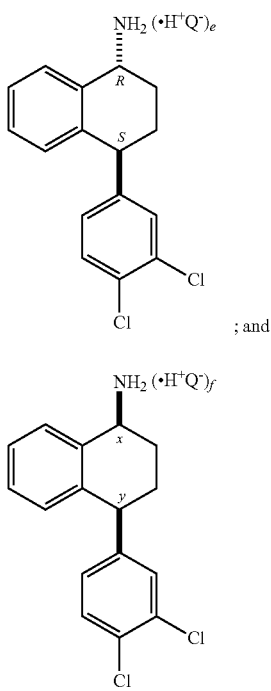

A

B in which e, f, x and y are as described above.

The mixtures set forth above are of use in pharmaceutical formulations. It is generally recognized that stereoisomers of bioactive compounds may have different properties. For example, the S-enantiomer of the beta-adrenergic blocking agent, propranolol, is known to be 100 times more potent than the R-enantiomer. However, potency is not the only concern in the field of pharmaceuticals. Optical purity is important since certain isomers may actually be deleterious rather than simply inert. Mixtures of diastereomers effectively combine and modulate the properties of each of the pure diastereomers. Thus, in selected embodiments, the invention provides mixtures of diastereomeric compounds A and B.

According to the present invention, a therapeutically effective amount of A or B, which may be a pure isomer or a mixture of any A and B, may also be administered to a person in need of therapy.

Disorders treatable with compounds prepared by the methods of the present invention include, but are not limited to, depression, major depressive disorder, bipolar disorder, chronic fatigue disorder, seasonal affective disorder, agoraphobia, generalized anxiety disorder, phobic anxiety, obsessive compulsive disorder (OCD), panic disorder, acute stress disorder, social phobia, fibromyalgia, neuropathic pain, posttraumatic stress disorder, premenstrual syndrome, menopause, perimenopause and male menopause.

In addition to their beneficial therapeutic effects, compounds prepared by methods of the present invention may provide the additional benefit of avoiding or reducing one or more of the adverse effects associated with conventional mood disorder treatments. Such side effects include, for example, insomnia, breast pain, weight gain, extrapyramidal symptoms, elevated serum prolactin levels and sexual dysfunction (including decreased libido, ejaculatory dysfunction and anorgasmia).

The compounds (and their mixtures) prepared by the methods of the present invention are also effective for treating disruptive behavior disorders, such as attention deficit disorder (ADD) and attention deficit/hyperactivity disorder (ADHD), which is in accordance with its accepted meaning in the art, as provided in the DSM-IV-TR™. These disorders are defined as affecting one's behavior resulting in inappropriate actions in learning and social situations. Although most commonly occurring during childhood, disruptive behavior disorders may also occur in adulthood.

The term "treating" when used in connection with the foregoing disorders means amelioration, prevention or relief from the symptoms and/or effects associated with these disorders and includes the prophylactic administration of a compound of formula A or B, a mixture thereof, or a pharmaceutically acceptable salt of either, to substantially diminish the likelihood or seriousness of the condition.

Pure compounds and mixtures prepared by the methods of the present invention are also effective for treating eating disorders. Eating disorders are defined as a disorder of one's appetite or eating habits or of inappropriate somatotype visualization. Eating disorders include, but are not limited to, anorexia nervosa; bulimia nervosa, obesity and cachexia.

Mood disorders, such as depressive disorders, e.g., dysthymic disorder or major depressive disorder; bipolar disorders, e.g., bipolar I disorder, bipolar II disorder, and cyclothymic disorder; mood disorder due to a general medical condition with depressive, and/or manic features; and substance-induced mood disorder can be treated using compounds and mixtures of the invention.

Anxiety disorders, such as acute stress disorder, agoraphobia without history of panic disorder, anxiety disorder due to general medical condition, generalized anxiety disorder, obsessive-compulsive disorder, panic disorder with agoraphobia, panic disorder without agoraphobia, posttraumatic stress disorder, specific phobia, social phobia, and substance-induced anxiety disorder are treatable with compounds and mixtures of the invention.

Compounds and mixtures prepared by methods of the invention are also effective for treating cerebral function disorders. The term cerebral function disorder, as used herein, includes cerebral function disorders involving intellectual deficits, and may be exemplified by senile dementia, Alzheimer's type dementia, memory loss, amnesia/amnestic syndrome, epilepsy, disturbances of consciousness, coma, lowering of attention, speech disorders, Parkinson's disease and autism.

The compounds and mixtures are also of use to treat schizophrenia and other psychotic disorders, such as catatonic, disorganized, paranoid, residual or differentiated schizophrenia; schizophreniform disorder; schizoaffective disorder; delusional disorder; brief psychotic disorder; shared psychotic disorder; psychotic disorder due to a general medical condition with delusions and/or hallucinations.

The compounds of formulae A and B are also effective for treating sexual dysfunction in both males and females. Disorders of this type include, for example, erectile dysfunction and orgasmic dysfunction related to clitoral disturbances.

Compounds and mixtures prepared by the methods of the present invention are also useful in the treatment of substance abuse, including, for example addiction to cocaine, heroin, nicotine, alcohol, anxiolytic and hypnotic drugs, *cannabis* (marijuana), amphetamines, hallucinogens, phenylcyclidine, volatile solvents, and volatile nitrites. Nicotine addiction includes nicotine addiction of all known forms, such as, for example, nicotine addiction resulting from cigarette, cigar and/or pipe smoking, as well as addiction resulting from tobacco chewing. In this respect, due to their activity as norepinephrine and dopamine uptake inhibitors, the compounds of the present invention can function to reduce the craving for the nicotine stimulus. Bupropion (ZYBAN®, GlaxoSmithKline, Research Triangle Park, N.C., USA) is a compound that has activity at both norepinephrine and dopamine receptors, and is currently available in the United States as an aid to smoking cessation treatment. As a benefit beyond the therapeutic activity of buproprion, however, the compounds of the present invention provide an additional serotonergic component.

Pure compounds and mixtures prepared by the methods of the present invention are also effective in the prophylaxis of migraine.

Compounds and mixtures prepared by the methods of the present invention are also useful in the treatment of pain disorders, including for example fibromyalgia, chronic pain, and neuropathic pain. The term "fibromyalgia" describes several disorders, all characterized by achy pain and stiffness in soft tissues, including muscles, tendons, and ligaments. Various alternative terms for fibromyalgia disorders have been used in the past, including generalized fibromyalgia, primary fibromyalgia syndrome, secondary fibromyalgia syndrome, localized fibromyalgia, and myofascial pain syndrome. Previously, these disorders were collectively called fibrositis or fibromyositis syndromes. Neuropathic pain disorders are thought to be caused by abnormalities in the nerves, spinal cord, or brain, and include, but are not limited to: burning and tingling sensations, hypersensitivity to touch and cold, phantom limb pain, postherpetic neuralgia, and chronic pain syndrome (including, e.g., reflex sympathetic dystrophy and causalgia).

The magnitude of a prophylactic or therapeutic dose of a compound of formulae A, B or mixtures thereof will vary with the nature and severity of the condition to be treated and the route of administration. The dose, and perhaps the dose frequency, will also vary according to the age, body weight and response of the individual patient. In general, the total daily dose ranges of compounds of the present invention will be from about 1 mg per day to about 500 mg per day, preferably about 1 mg per day to about 200 mg per day, in single or divided doses. Dosages of less than 1 mg per day of compounds of the invention are also within the scope of the instant invention.

Any suitable route of administration may be employed. For example, oral, rectal, intranasal, and parenteral (including subcutaneous, intramuscular, and intravenous) routes may be employed. Dosage forms can include tablets, troches, dispersions, suspensions, solutions, capsules and patches.

Pharmaceutical compositions of the present invention include as active ingredient, a single compound, or a mixture of compounds, of formula A or B, or a pharmaceutically acceptable salt of A or B, together with a pharmaceutically acceptable carrier and, optionally, with other therapeutic ingredients.

The pharmaceutically acceptable carrier may take a wide variety of forms, depending on the route desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Exemplary formulations, are well known to those skilled in the art, and general methods for preparing them are found in any standard pharmacy school textbook, for example, Remington, THE SCIENCE AND PRACTICE OF PHARMACY, 21st Ed., Lippincott.

Thus, as set forth herein, the invention is exemplified by the following aspects and embodiments.

A method for converting an oxime into an enamide. The method includes, (a) contacting the oxime with a phosphine and an acyl donor, under conditions appropriate to convert the oxime into the enamide.

The method according to the preceding paragraph in which the oxime has the formula:

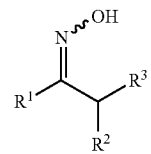

wherein $R^1$, $R^2$ and $R^3$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. At least two of $R^1$, $R^2$ and $R^3$ are optionally joined to form a ring system selected from substituted or unsubstituted cycloalkyl, substituted or unsubstituted heterocycloalkyl, substituted or unsubstituted aryl and substituted or unsubstituted heteroaryl.

The method of any of the preceding paragraphs in which the oxime has the formula:

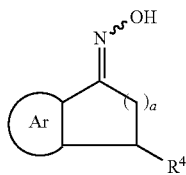

wherein Ar is a member selected from substituted or unsubstituted aryl and substituted or unsubstituted heteroaryl. $R^4$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and, the index a is selected from the integers from 1 to 4.

The method of any of the preceding paragraphs in which $R^4$ is substituted or unsubstituted aryl.

The method of any of the preceding paragraphs in which $R^4$ is substituted or unsubstituted phenyl.

The method of any of the preceding paragraphs in which $R^4$ is phenyl substituted with at least one halogen.

The method of any of the preceding paragraphs in which $R^4$ has the formula:

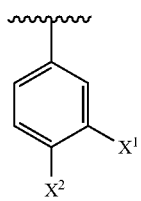

wherein $X^1$ and $X^2$ are independently selected halo moieties.

The method of any of the preceding paragraphs in which $X^1$ and $X^2$ are each chloro.

The method of any of the preceding paragraphs in which Ar is substituted or unsubstituted phenyl.

The method of any of the preceding paragraphs in which the oxime has the formula:

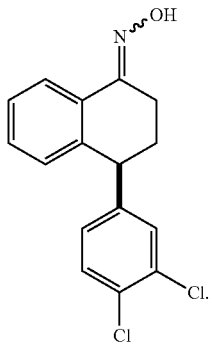 [SMILES: ON=C1CC[C@@H](c2ccc(Cl)c(Cl)c2)c2ccccc21]

The method of any of the preceding paragraphs in which acyl donor has the formula: $Z—C(O)—R^5$, wherein Z is a leaving group. $R^5$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

The method according any of the preceding paragraphs in which Z has the formula:

$R^6—C(O)—O—$ wherein $R^6$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

The method according to any of the preceding paragraphs in which both $R^5$ and $R^6$ are independently selected substituted or unsubstituted $C_1$-$C_4$ moieties.

The method according to any of the preceding paragraphs in which the phosphine has the formula:

$P(Q)_3$ wherein each Q is a member independently selected from H, substituted or unsubstituted alkyl and substituted or unsubstituted aryl.

The method according to any of the preceding paragraphs in which each Q is a member independently selected from substituted or unsubstituted $C_1$-$C_6$ alkyl.

The method according to any of the preceding paragraphs in which the contacting is in solution with an aprotic solvent.

The method according to any of the preceding paragraphs in which the aprotic solvent is an aromatic solvent.

The method according to any of the preceding paragraphs in which the aprotic aromatic solvent is selected from toluene, xylene and combinations thereof.

The method according to any of the preceding paragraphs in which enamide has the formula:

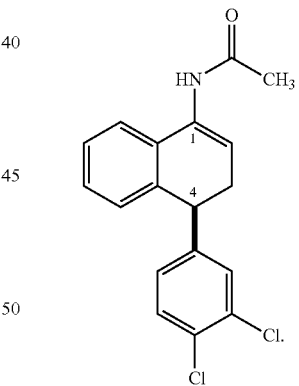

The method according to any of the preceding paragraphs in which C-4 has a configuration selected from R, S and mixtures thereof.

The method according to any of the preceding paragraphs in which C-4 is of S configuration.

The method according to any of the preceding paragraphs further including: (b) contacting the enamide formed in step (a) with a hydrogenation catalyst and hydrogen or hydrogen transfer reagent under conditions appropriate to hydrogenate a carbon-carbon double bond of the enamide, thereby converting the enamide to an amide.

The method according to any of the preceding paragraphs in which the catalyst is a chiral catalyst.

The method according to any of the preceding paragraphs in which the chiral catalyst is a complex of a transition metal with a chiral phosphine ligand.

The method according to any of the preceding paragraphs in which the amide is a racemic or chiral amide.

The method according to any of the preceding paragraphs in which amide has the formula:

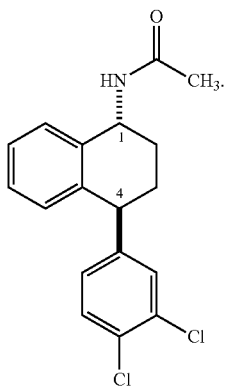 [SMILES: CC(=O)N[C@@H]1CC[C@@H](c2ccc(Cl)c(Cl)c2)c2ccccc21]

The method according to any of the preceding paragraphs in which C-1 and C-4 have a configuration independently selected from R and S.

The method according to any of the preceding paragraphs in which C-1 is of R configuration; and C-4 is of S configuration.

The method according to any of the preceding paragraphs further including: (c) contacting the amide with a deacylating reagent under conditions appropriate to deacylate —HNC(O)R$^5$ of the amide, thereby forming an amine.

The method according to any of the preceding paragraphs including: (d) isolating said amine.

The method according to any of the preceding paragraphs in which isolating comprises selective crystallization.

The method according to any of the preceding paragraphs in which the amine has the formula:

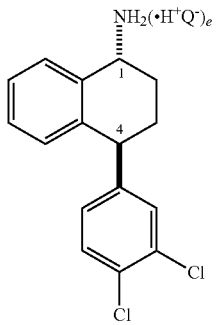

wherein Q$^-$ is an anion; and e is 0 to 1.

The method according to any of the preceding claims in which C-1 and C-4 have a configuration independently selected from R and S.

The method according to any preceding claims in which C-1 is of R configuration; and C-4 is of S configuration.

A method of converting an oxime having the formula

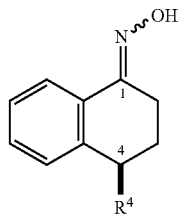

into an enamide having the formula:

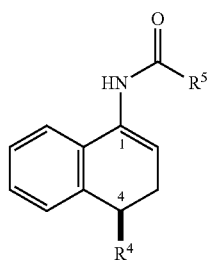

wherein R$^4$ is selected from substituted or unsubstituted aryl and substituted or unsubstituted heteroaryl. R$^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl. The method includes: (a) contacting the oxime with a phosphine and an acyl donor under conditions appropriate to convert the oxime to the enamide.

The method according to the preceding paragraph in which C-4 is of S configuration.

The method according to the preceding paragraphs in which the phosphine is a trialkylphosphine.

The method according to the preceding paragraphs in which the oxime, the acyl donor and the phosphine are dissolved in an aromatic solvent.

The method according to the preceding paragraphs in which the acyl donor is an alkyl anhydride.

The method according to the preceding paragraphs including: (b) contacting the enamide formed in step (a) with a chiral hydrogenation catalyst and hydrogen under conditions appropriate to hydrogenate a carbon-carbon double bond conjugated to C(O) of the enamide, thereby converting the enamide to an amide having the formula:

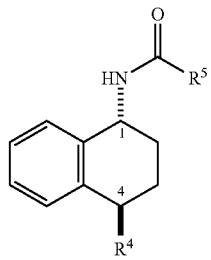

wherein C-1 has a configuration selected from R and S.

The method according to the preceding paragraphs in which the chiral catalyst includes rhodium complexed to a chiral phosphine ligand.

The method according to the preceding paragraphs further including: (c) contacting the amide with a deacylating reagent under conditions appropriate to deacylate —HNC(O)R⁵ of the amide, thereby forming an amine having the formula:

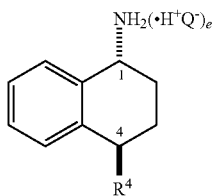

wherein Q⁻ is an anion. The index e is 0 or 1.

The method according to the preceding paragraphs in which the deacylating reagent is an enzyme.

The method according to the preceding paragraphs in which the deacylating reagent is an acid.

A mixture comprising:

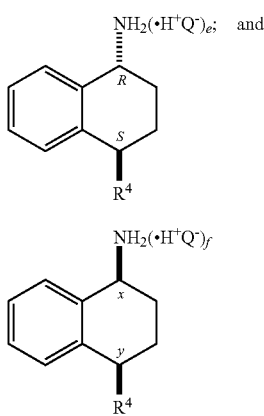

wherein R⁴ is a member selected from substituted or unsubstituted aryl and substituted or unsubstituted heteroaryl. Q⁻ is an anion. The indices e and f are independently selected numbers from 0 to 1; and x and y are selected from R and S, such that when x is R, y is R, and when x is S, y is S.

The mixture according to the preceding paragraph in which A is present in the mixture in a diastereomeric excess of at least 90% relative to B.

The mixture according to the preceding paragraphs in which A is present in said mixture in a diastereomeric excess of at least 98% relative to B.

The mixture according to the preceding paragraphs in which x and y are R.

The mixture according to the preceding paragraphs in which x and y are S.

The mixture according to the preceding paragraphs in which R⁴ is substituted or unsubstituted phenyl.

A pharmaceutical formulation including a mixture according to the preceding paragraphs.

The following examples are provided to illustrate selected embodiments of the invention and are not to be construed as limiting its scope.

EXAMPLES

Example 1

Synthesis of N—((S)-4-(3,4-dichlorophenyl)-3,4-dihydronaphthalen-1-yl)acetamide (3)

1.1. Synthesis of Oxime 2

A suspension formed from a mixture of(S)-tetralone 1 (56.0 g, 0.192 mol), hydroxylamine hydrochloride (14.7 g, 0.212 mol), and sodium acetate (17.4 g, 0.212 mol) in methanol (168 mL) was heated to reflux for 1 to 5 hours under a $N_2$ atmosphere. The progress of the reaction was monitored by HPLC. After the reaction was complete, the reaction mixture was concentrated in vacuo. The residue was diluted with toluene (400 mL) and 200 mL water. The organic layer was separated and washed with an additional 200 mL water. The organic layer was concentrated and dried to give crude solid oxime 2 (58.9 g, 100%), m. p. 117-120° C.

$^1$H NMR (400 MHz, CDCl$_3$) δ (ppm) 9.17 (br, 1H, OH), 7.98 (m, 1H), 7.36 (d, 1H, J=8.0 Hz), 7.29 (m, 2H), 7.20 (d, 1H, J=2.4 Hz), 6.91 (m, 2H), 4.11 (dd, 1H, J=7.2 Hz, 4.4 Hz), 2.82 (m, 2H), 2.21 (m, 1H), 2.08 (m, 1H). $^{13}$C NMR (100 MHz, CDCl$_3$) δ 154.94, 144.41, 140.40, 132.83, 130.92, 130.82, 130.68, 130.64, 129.98, 129.38, 128.12, 127.64, 124.48, 44.52, 29.51, 21.27.

1.2. Synthesis of Enamide 3

The solution of the crude oxime 2 (59 g, 0.193 mol) in toluene (500 mL) was purged with $N_2$ for 30 min. Et$_3$P (25 g, 0.212 mol) was charged. After stirring for 10 min, acetic anhydride (21.6 g, 20 mL, 0.212 mol) was added. The reaction mixture was refluxed for 8 to 13 h. Progress of the reaction was monitored by HPLC. The reaction mixture was cooled to room temperature. 6N NaOH (aq) (86 mL, 0.516 mol) and 1.0 M (n-Bu)$_4$NOH in methanol (1.0 mL) were added. The hydrolysis was complete in about 2 to 4 h. The organic layer was separated and diluted with EtOAc (300 mL) and 2-BuOH (30 mL). The diluted organic solution was washed with 1% HOAc (aq) solution (300 mL) and DI water (3×300 mL) and concentrated to about 350 mL of a slurry in vacuo. The slurry was diluted with heptane (100 mL) and 2-BuOH (4 mL) and heated to reflux to form a clear solution. Heptane (50 to 200 mL) was slowly added until a cloudy solution formed. The suspension was slowly cooled to rt. The product was filtered out, washed with 30% toluene and 70% heptane (3×100 mL) solution and dried in a vacuum oven to give 56.9 g white solid (enamide 3, 89% yield), m. p. 167-168° C.

(S)-Tetralone 1 (50.0 g, 0.172 mol) was slurried in methanol (150 mL) with hydroxylamine hydrochloride (13.1 g, 0.189 mol) and sodium acetate (15.5 g, 0.189 mol). The resulting suspension was heated to reflux for 2 to 6 h under an inert atmosphere with progress monitored by HPLC. On completion, the mixture was cooled to 25° C., diluted with toluene (300 mL) and quenched with 1.7 N NaOH (100 mL). The mixture was concentrated in vacuo under reduced pressure, the aqueous layer removed and the organic layer washed further with DI water (100 mL). Further toluene (300 mL) was charged to the vessel and water removed by azeotropic distillation. Once at ambient temperature, n-Bu$_3$P (47.1 mL, 0.183 mol) was charged to the reactor, followed by acetic anhydride (32.5 mL, 0.344 mol). The reaction was heated to reflux and monitored by HPLC. After 20-24 h, the reaction was cooled to ambient temperature and quenched with 6 N NaOH (120 mL). This mixture was allowed to react for 2 to 6 h before the aqueous layer was removed. The organic phase was washed with DI water (100 mL). Concentration of the mixture in vacuo, cooling to room temperature and diluting with isopropanol (50 mL) was done prior to addition of heptane to assist with crystallization. An initial charge of heptane (50 mL) was followed by an additional 650 mL. Aging of the slurry followed by filtration, washing (4×100 mL heptane) and drying yielded a light yellow solid (enamide 3, 44.1 g, 77%).

$^1$H NMR (400 MHz, CDCl$_3$) δ (ppm) 7.35 (d, 1H, J=8.4 Hz), 7.26 (m, 3H), 7.17 (m, 1H), 7.05 (dd, 1H, J=8.0, 1.6 Hz), 7.00 (br, 1H), 6.87 (m, 0.82H, 82% NH rotamer), 6.80 (br, 0.18H, 18% NH rotamer), 6.31 (t, 0.82H, J=4.8 Hz, 82% H rotamer), 5.91 (br, 0.18H, 18% H rotamer), 4.12 (br, 0.18H, 18% H rotamer), 4.03 (t, 0.82H, J=8.0 Hz, 82% H rotamer), 2.72 (m, 1H), 2.61 (ddd, 1H, J=16.8, 8.0, 4.8 Hz), 2.17 (s, 2.46H, 82% CH$_3$ rotamer), 1.95 (s, 0.54H, 18% CH$_3$ rotamer). 100 MHz $^{13}$C NMR (CDCl$_3$) δ 169.3, 143.8, 137.7, 132.3, 131.8, 131.4, 130.5, 130.3, 130.2, 128.8, 128.1, 127.8, 127.2, 123.8, 122.5, 121.2, 117.5, 42.6, 30.3, 24.1.

Example 2

Synthesis of N-((1R,4S)-4-(3,4-dichlorophenyl)-1,2,3,4-tetrahydronaphthalen-1-yl)acetamide (4)

The enamide 3 (24 g, 72 mmol) was slurried in degassed isopropanol (200 mL). The resulting slurry was transferred to the appropriate reactor. Prior to the addition of the catalyst solution, the content of the reactor was purged with nitrogen. A solution of (R,R)-MeBPE(COD)RhBF$_4$ catalyst (20.1 mg, 0.036 mmol, 0.05 mol %) in isopropanol (IPA) (100 mL) was added to the reactor. The content was cooled to 0° C. and purged with nitrogen three times. The reactor was then purged with hydrogen and pressurized to 90 psig. The reaction was aged with agitation at 0° C. for 7.5 h and conversion was monitored by the hydrogen uptake. The content was then warmed to RT and hydrogen was vented. After purging with nitrogen, the contents were drained. The reaction mixture was heated to 50° C. and filtered through a pad of Celite. The clear orange solution was concentrated to ~50% volume (150 mL) and diluted with toluene (5.9 g, 5 wt %). The suspension was heated to 65° C. and water (14.7 mL) was added dropwise to form a cloudy solution. The slurry was slowly cooled to −10° C. and aged for 30 minutes. The solid was filtered and washed with cold IPA (2×45 mL). The cake was dried under vacuum at 45° C. overnight to afford 20.0 g (83% yield) of trans acetamide 4 (>99% de).

$^1$H NMR (CDCl$_3$) 400 MHz δ 7.34 (dd, 2H, J=7.9, 2.4 Hz), 7.23 (t, 1H, J=7.5 Hz), 7.15 (m, 2H), 6.85 (dd, 1H, J=8.2, 2.0 Hz), 6.82 (d, 1H, J=7.7 Hz), 5.72 (d, 1H, J=8.4 Hz), 5.31 (dd, 1H, J=13.2, 8.1 Hz), 4.10 (dd, 1H, J=7.0, 5.9 Hz), 2.17 (m, 2H), 2.06 (s, 3H), 1.87 (m, 1H). 1.72 (m, 1H); $^{13}$C NMR (CDCl$_3$) 100 MHz δ 169.7, 146.9, 138.8, 137.7, 132.6, 130.8, 130.6, 130.5, 130.3, 128.4, 128.3, 127.9, 127.4, 47.9, 44.9, 30.5, 28.4, 23.8.

Example 3

Synthesis of (1R,4S)-4-(3,4-dichlorophenyl)-1,2,3,4-tetrahydronaphthalen-1-amine hydrochloride (5)

A solution of trans-acetamide 4 (9.0 g, 26.9 mmol), n-propanol (45 mL) and 5M hydrochloric acid (45 mL) was refluxed for approximately 48 h (90-93° C.). During this time, the reaction temperature was maintained at ≥90° C. by periodically collecting the distillate until the reaction temperature was >92° C. Additional n-propanol was added periodically to maintain the solution at its original volume. After the hydrolysis was complete, the solution was slowly cooled to 0° C., resulting in a slurry, which was aged for one hour at 0° C. The reaction mixture was filtered, and the cake was washed with 1:1 methanol/water (20 mL), followed by t-butyl methyl ether (20 mL). The wet-cake was dried under vacuum at 45 to 50° C. to afford 7.0 g of the amine hydrochloride 5 (80% yield).

$^1$H NMR (DMSO-d$_6$) δ 1.81-1.93 (m, 2H), 2.12-2.21 (m, 1H), 2.28-2.36 (m, 1H), 4.28 (t, 1H, J=6.8), 4.59 (br.s, 1H), 6.84 (d, 1H, J=7.6), 7.05 (dd, 1H, J=8.4, 1.6), 7.25 (t, 1H, J=7.6), 7.32 (t, 1H, J=7.6), 7.37 (d, 1H, J=1.6), 7.56 (d, 1H, J=8.4), 7.76 (d, 1H, J=7.2), 8.80 (br.s, 3H); $^{13}$C NMR (DMSO-d$_6$) 147.4, 138.9, 133.6, 131.0, 130.5, 130.4, 130.1, 129.0, 128.9, 128.4, 128.2, 126.8, 47.9, 43.1, 27.8, 25.2.

Example 4

In Situ Formation/Acylation of Oxime

Oxime 2 was acylated in situ to afford the intermediate 2A, which undergoes reductive acylation to provide a mixture of the acylated enamide 3 and the diacylated analog 3A. The reaction was carried out in either toluene or o-xylene at reflux. The mixture of 3 and 3A was then treated with an aqueous solution of base such as sodium hydroxide or sodium carbonate, with or without a phase transfer catalyst (e.g. tetrabutylammonium hydrogen sulfate/hydroxide), to convert the intermediate 3A to the desired enamide 3. Exemplary reaction conditions for the conversion of oxime 2 to enamide 3 are shown in Schemes 3a and 3b.

Scheme 3a

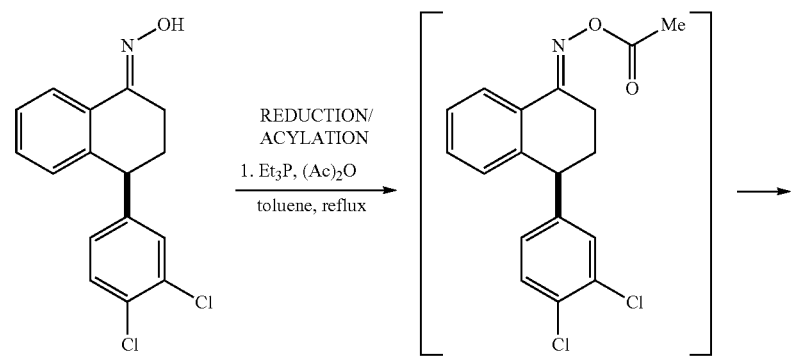

-continued
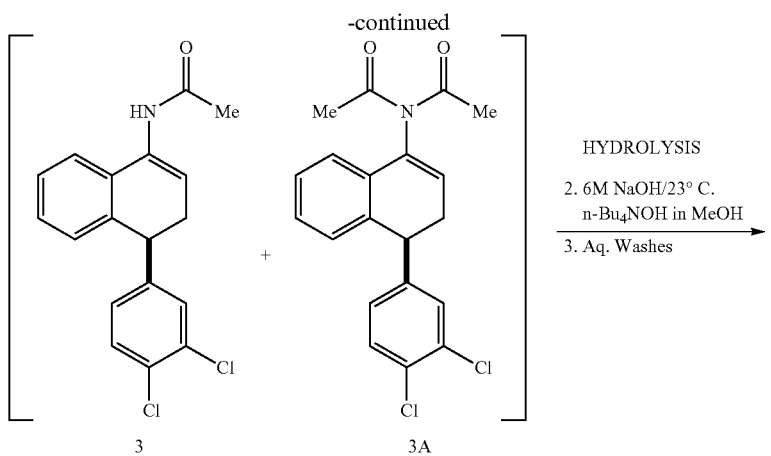
HYDROLYSIS
2. 6M NaOH/23° C.
n-Bu₄NOH in MeOH
3. Aq. Washes
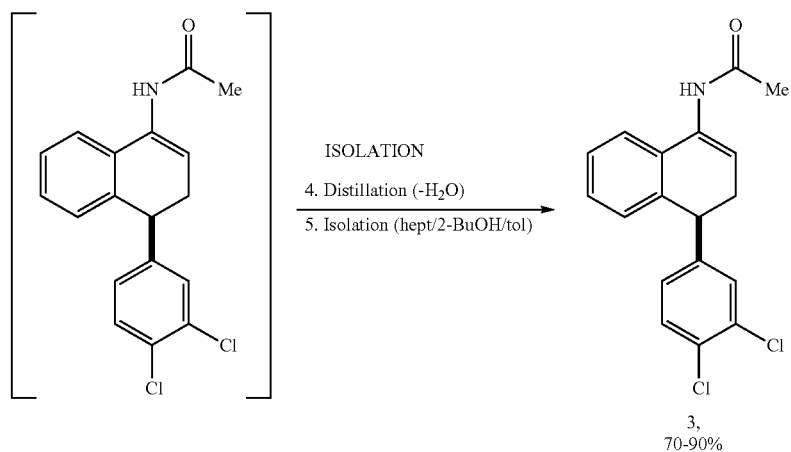
ISOLATION
4. Distillation (-H₂O)
5. Isolation (hept/2-BuOH/tol)
3, 70-90%
Scheme 3b
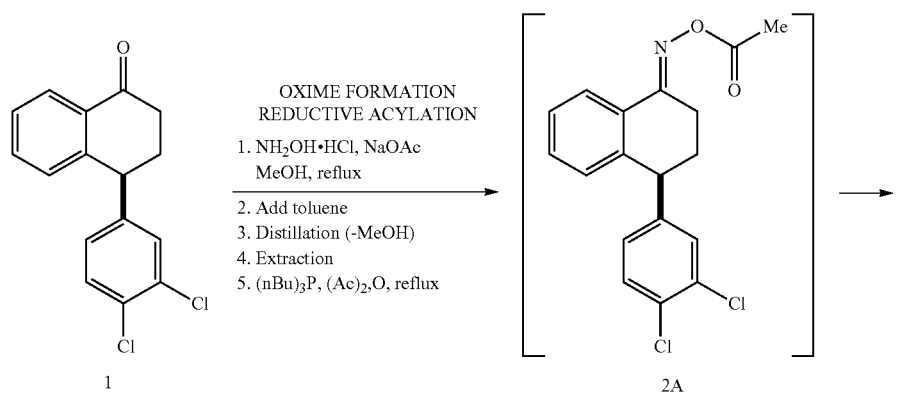
OXIME FORMATION
REDUCTIVE ACYLATION
1. NH₂OH•HCl, NaOAc
MeOH, reflux
2. Add toluene
3. Distillation (-MeOH)
4. Extraction
5. (nBu)₃P, (Ac)₂O, reflux

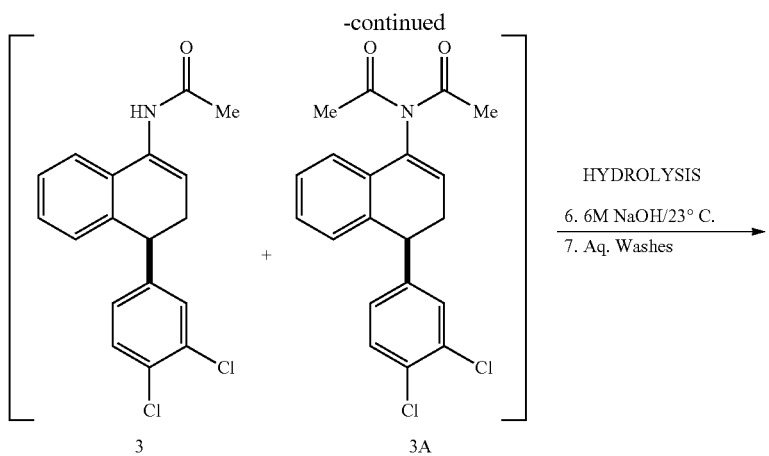

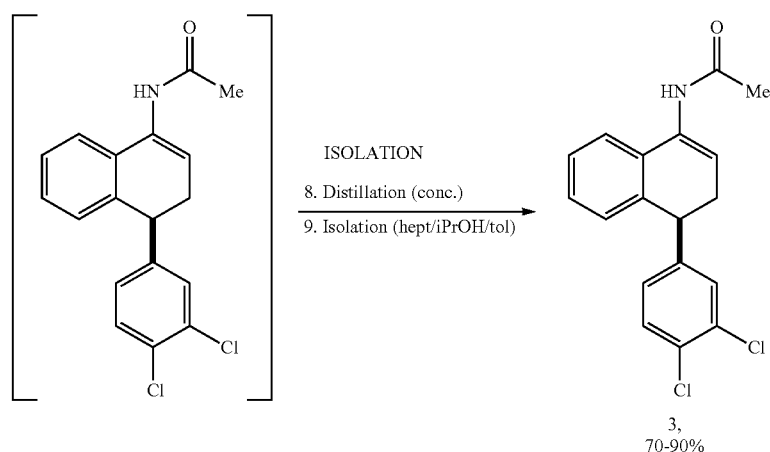

Example 5

Catalytic Asymmetric Hydrogenation of the Enamide 3 Using (R,S,R,S)-MePennPhos(COD)RhBF$_4$ as the Catalyst As shown in Scheme 4, the enamide 3 was subjected to homogeneous catalytic asymmetric hydrogenation in the presence of a chiral catalyst, H$_2$, and a solvent. In this example the catalyst was derived from the complex of the transition metal rhodium with the chiral phosphine ligand, (1R,2S,4R,5S)—P,P-1,2-phenylenebis {(2,5-endo-dimethyl)-7-phosphabicyclo[2.2.1]heptane}(R,S,R,S-MePennPhos). The hydrogenations were carried out at a substrate concentration of about 0.12 M to about 0.24 M of compound 3.

Scheme 4

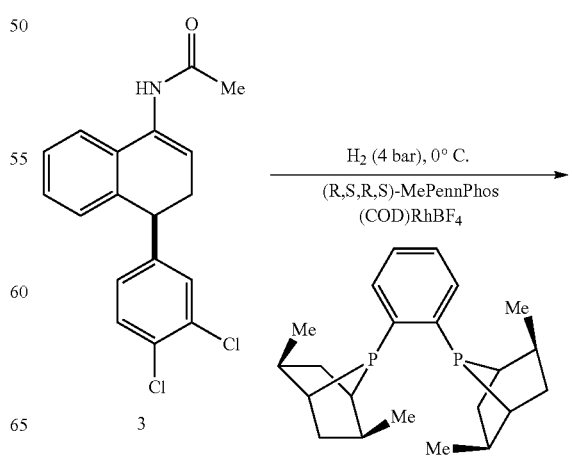

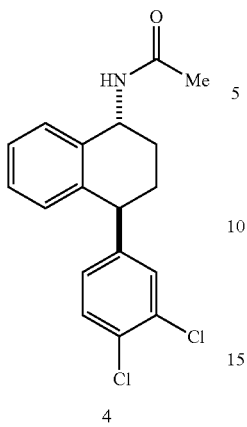

4

Example 6

Catalytic Asymmetric Hydrogenation of the Enamide 3 Using (R,R)-MeBPE Rh(COD)BF$_4$ as the Catalyst As shown in Scheme 5, the enamide 3 was subjected to homogeneous catalytic asymmetric hydrogenation in the presence of a chiral catalyst, H$_2$, and a solvent. In this example the catalyst was derived from the complex of the transition metal rhodium with the chiral phosphine ligand, (R,R)-1,2-bis(2,5-dimethylphospholano)ethane (R,R-MeBPE). The hydrogenations were carried out in the concentration range of about 0.12 M to about 0.24 M relative to the substrate 3.

Scheme 5

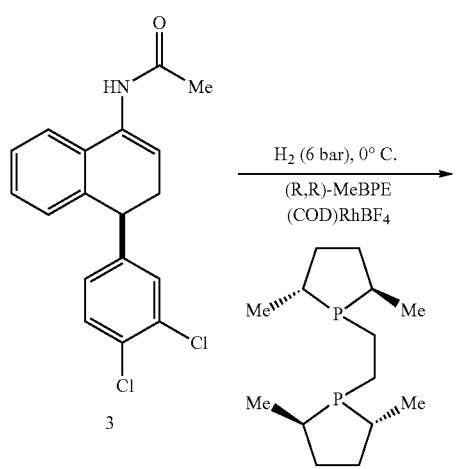

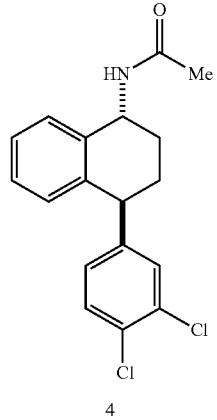

4

Example 7

Asymmetric Hydrogenation Catalyzed by (R,R)-Norphos(COD)RH—BF$_4$

A slurry of the (S)-enacetamide, N—((S)-4-(3,4-dichloropheyl)-3,4-dihydronaththalen-1-yl)acetamide (60.4 g, 0.18 mol), in isopropanol (595.0 g) was purged of oxygen with vacuum/nitrogen cycles. The homogeneous catalyst precursor (referred to as a "catalyst"), (R,R)-Norphos(COD)RH—BF4 was added as a solution in methanol (34.6 mg, 0.025 mol %, 0.53 mL). After purging the system with hydrogen several times, the vessel was filled with hydrogen at the desired reaction pressure (approx 7 bar). The mixture was stirred at 25° C. and reaction progress was monitored by hydrogen uptake. Once the reaction was judged to be complete (hydrogen uptake and HPLC), the pressure was released and the system was purged repeatedly with nitrogen. The light yellow slurry was diluted with isopropanol (194.7 g), heated to dissolution (65° C.) and polish filtered. The mixture was heated to reflux to dissolve all solids. The solution was slowly cooled to 60-65° C. at which time the product crystallized. The antisolvent, water (262 g), was added at about 60-65° C., then the mixture was cooled to 0° C. over two hours and held at that temperature for aging. Filtration of the lightly colored solid was followed by washing with cold isopropanol (2×61 g). Drying of the off white solid under reduced pressure at 50-55° C. provided the (1R,4S)-acetamide in 99% de (56.6 g, 93% yield).

Example 8

Oxime and Enamide Formation

Chiral (4S)-tetralone (100.0 g, 0.34 mol) was reacted with hydroxylamine hydrochloride (28.7 g, 0.41 mol) and sodium acetate (33.8 g, 0.41 mol) in toluene (1.37 L) for approximately 2 h at 103° C. Water was removed from the reaction mixture by azeotropic distillation. The reaction was quencher at 25° C. with 2 N sodium hydroxide (167.0 g). The aqueous phase was separated and the organic phase was washed once with water (400.0 g). Toluene (700.0 g) was added was added and the resulting organic solution, containing the oxime, was dried by azeotropic distillation under reduced pressure to the desired reaction concentration. Triethylphosphine (89.0 g, 0.38 mol, 50 wt % in toluene) is added, followed by addition of acetic anhydride (38.5 g, 0.38 mol), which afforded the oxime acetate intermediate. The reaction mixture was allowed to react at reflux (112-113° C.) until the remaining oxime acetate is <2% of the product, as determined by HPLC. The reaction mixture was cooled to 20-25° C. and the minor enimide by-product was hydrolyzed (to enacetamide) using 6 N sodium hydroxide (210 g) in conjunction with the phase transfer reagent, tertbutylammonium hydroxide (5.0 g). The biphasic mixture was allowed to phase separate and the aqueous phase was discarded. The organic phase was washed with 0.5% acetic acid aqueous solution (67° C., 600.0 g). The aqueous phase was removed and the organic phase was washed once with water (67° C., 600.0 g) to remove inorganic salts. The organic phase was concentrated and the warm solution was polish filtered to remove additional inorganic salts. Heptanes (150 g) and 2-butanol (7.0 g) were added and the slurry was heated to 100° C. in order to achieve dissolution. The solution was cooled to approximately 85° C. to initiate crystallization. Additional heptanes (190 g) were added to the slurry at 85° C., and the mixture was then cooled to 0° C. The slurry was aged at 0° C. for 15 min., then filtered and washed three times with a solution consisting of a mixture of heptanes and toluene (125 g). The product was vacuum dried at 35-45° C. 17.8 g (89% yield) of a white crystalline solid, (S)-enacetamide was recovered.

The method according to this example was applied to a number of substrates, the results of which are set forth in Table 1.

TABLE 1

| | | Oximes and Enamides Produced | | |
|---|---|---|---|---|
| Entry | Oxime, yield | | Enamide reaction time | Enamide, yield |
| 1 | 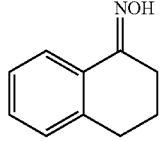 Quantitative | | 16.5 h | 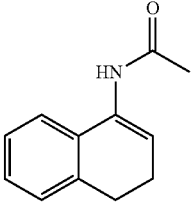 89% |
| 2 | 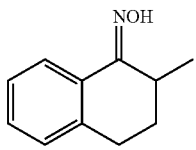 Quantitative | | 22 h | 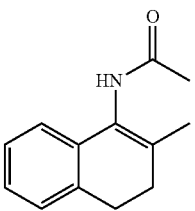 74% |
| 3 | 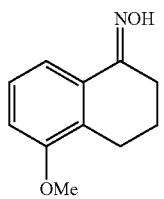 97% | | 23 h | 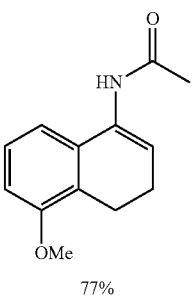 [SMILES: COc1cccc2c1CCC=C2NC(C)=O] 77% |
| 4 | 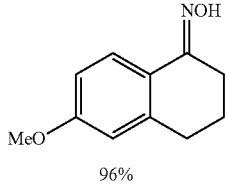 96% | | 19 h | 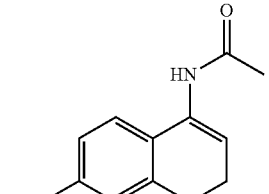 71% |

TABLE 1-continued
Oximes and Enamides Produced
| Entry | Oxime, yield | Enamide reaction time | Enamide, yield |
|---|---|---|---|
| 5 | 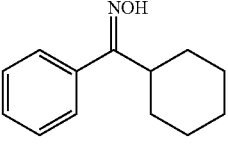 Quantitative | 24 h | 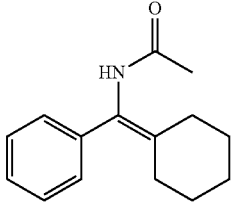 90% |
| 6 | 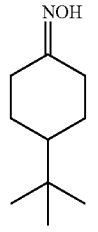 99.8% | 21.5 h | 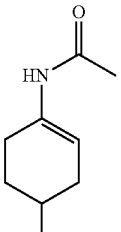 71% |
| 7 | 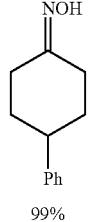 99% | 21.5 h | 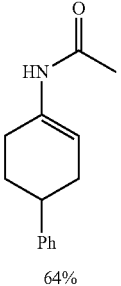 [SMILES: CC(=O)NC1=CCC(c2ccccc2)CC1] 64% |
| 8 | 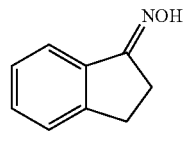 93% | 5.3 h | 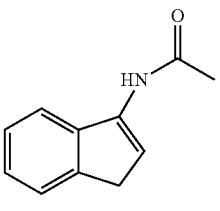 78% |
| 9 | 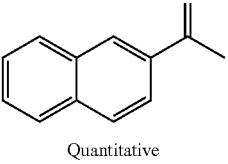 Quantitative | 10 h | 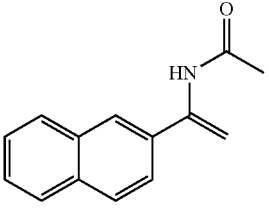 76% |

TABLE 1-continued

Oximes and Enamides Produced

| Entry | Oxime, yield | Enamide reaction time | Enamide, yield |
|---|---|---|---|
| 10 | propiophenone oxime; Quantitative | 10 h | N-(1-phenylprop-1-en-1-yl)acetamide; 58% |
| 11 | isobutyrophenone oxime; 99% | 22.5 h | N-(2-methyl-1-phenylprop-1-en-1-yl)acetamide; 58% |
| 12 | 3-(hydroxyimino)-2-phenylbutanenitrile; 98% | 28 h | N-(3-cyano-3-phenylbut-2-en-2-yl)acetamide; 54% |
| 13 | 2-methylcyclohexanone oxime; Quantitative | <22 h | N-(2-methylcyclohex-1-en-1-yl)acetamide; 54% |

Example 9

Amide Deprotection

A solution of (1R,4S)-acetamide in dry THF (212.7 g, 239.3 mL) was treated with dry pyridine (8.7 g, 8.9 mL, 110 mmol). The resulting clear, colorless solution was cooled to approximately 0 OC. Oxalyl chloride (12.9 g, 8.9 mL, 101.6 mmol) was added dropwise to the stirred solution, with care to control the exotherm and effervescence of CO and $CO_2$. The addition of the activating reagent was accompanied by the formation of a slurry. The slurry was allowed to stir cold for a short period (approx. 15 min) prior to sampling for conversion assessment. Once the reaction was complete, dry propylene glycol was added to the reaction, resulting in a minor exotherm. The reaction was warmed to 25° C., during which time the slurry changed in color and consistency. HPLC analysis of a second sample showed completion before the addition of 1-propanol (96.9 g, 120.5 mL). 6N HCl (128.0 g, 120.0 mL) was added. The mixture was heated to effect dissolution and the resulting mixture was polish filtered. THF was removed by atmospheric distillation. After concentration of the mixture, it was slowly cooled to 3° C. The resulting lightly colored slurry was filtered to yield and off-white cake. The cake was first washed with 17 wt % n-PrOH in deionized water (72.6 g, 75 mL total) and then with cold mtBE (55.5 g, 75 mL). The off-white wet cake was dried under vacuum at 45-50° C. The product was recovered as an off-white to white solid (24.8 g, 84.1% yield) with excellent purity (>99% purity by HPLC).

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed:

1. A process for preparing a single trans enantiomer of formula

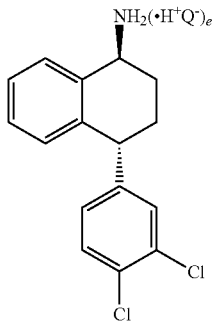

wherein Q⁻ is an anion; and e is 0 or 1, said process comprising:

a) reacting a ketone of formula:

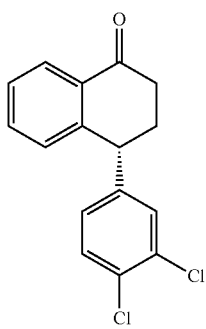 [SMILES: O=C1CC[C@H](c2ccc(Cl)c(Cl)c2)c2ccccc21]

with hydroxylamine to form an oxime of formula:

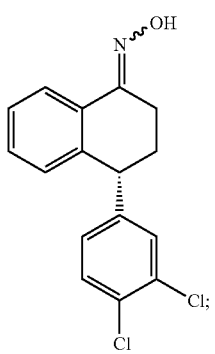 [SMILES: ON=C1CC[C@H](c2ccc(Cl)c(Cl)c2)c2ccccc21]

b) reacting said oxime with acetic anhydride in the presence of a trialkylphosphine to produce an enamide of formula:

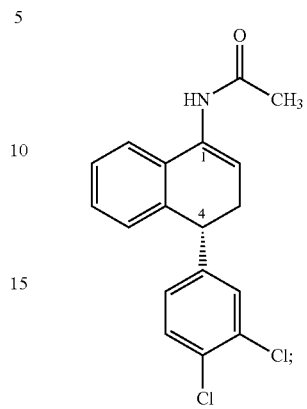

c) reducing said enamide with hydrogen in the presence of a chiral rhodium catalyst to produce a trans acetamide isomer of formula:

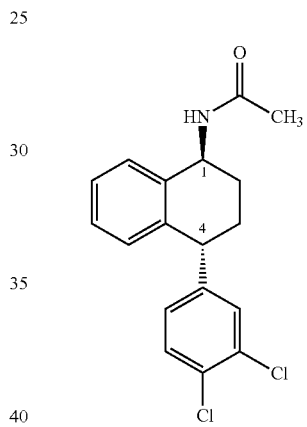

containing less than 10% of the corresponding cis isomer; and d) hydrolyzing said trans acetamide isomer.

2. A process according to claim 1 wherein reacting the ketone with hydroxylamine further includes reacting with sodium acetate in methanol.

3. A process according to claim 1 wherein the chiral rhodium catalyst is a complex of rhodium with a chiral phosphine ligand.

4. A process according to claim 1 wherein hydrolyzing includes acid hydrolysis.

5. A process according to claim 4 wherein the acid hydrolysis includes hydrolyzing with hydrochloric acid.

6. A process according to claim 1 wherein Q⁻ is chlorine.

* * * * *